(12) United States Patent
Bhide

(10) Patent No.: US 7,053,223 B2
(45) Date of Patent: May 30, 2006

(54) INHIBITORS OF FARNESYL PROTEIN TRANSFERASE

(75) Inventor: Rajeev S. Bhide, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 50 days.

(21) Appl. No.: 10/775,438

(22) Filed: Feb. 10, 2004

(65) Prior Publication Data

US 2004/0181068 A1 Sep. 16, 2004

Related U.S. Application Data

(60) Provisional application No. 60/447,513, filed on Feb. 14, 2003.

(51) Int. Cl.
*C07D 233/02* (2006.01)
(52) U.S. Cl. .................. 548/311.4; 546/280.4
(58) Field of Classification Search ......... 514/337, 514/397; 548/311.4; 546/280.4
See application file for complete search history.

(56) References Cited

U.S. PATENT DOCUMENTS 5,639,778 A * 6/1997 Andersson et al. ......... 514/411

OTHER PUBLICATIONS

Crul et al Phase I Clinical and Pharmacologic Study of Chronic Oral Administration of ht Parnesyl Protein Transferase Inhibitor R115777 in Advanced Cancer J. clinical Oncology, 20(11), Jun. 1, 2002, 2726-2735.*

* cited by examiner

*Primary Examiner*—Amelia A. Owens
(74) *Attorney, Agent, or Firm*—Maureen S. Gibbons

(57) ABSTRACT

The present invention discloses the identification of the novel inhibitors of farnesyl protein transferase and ras protein farnesylation. The compounds and pharmaceutical compositions disclosed herein are useful in treating diseases associated with farnesyl protein transferase, such as cancer.

9 Claims, No Drawings

INHIBITORS OF FARNESYL PROTEIN TRANSFERASE

RELATED APPLICATIONS

This application claims priority benefit under Title 35 §119(e) of U.S. provisional Application No. 60/447,513, filed Feb. 14, 2003, the contents of which are herein incorporated by reference.

FIELD OF THE INVENTION

This invention relates to compounds that inhibit farnesyl-protein transferase and ras protein farnesylation, thereby making them useful as anti-cancer agents. The compounds are also useful in the treatment of diseases, other than cancer, associated with signal transduction pathways operating through ras and those associated with CAAX-containing proteins other than ras that are also post-translationally modified by the enzyme farnesyl protein transferase. The compounds also act as inhibitors of other prenyl transferases, and thus be effective in the treatment of diseases associated with other prenyl modifications of proteins.

BACKGROUND OF THE INVENTION

The mammalian ras gene family comprises three genes: H-ras, K-ras and N-ras. The ras proteins are a family of GTP-binding and hydrolyzing proteins that regulate cell growth and differentiation. Overproduction of normal ras proteins or mutations that inhibit their GTPase activity can lead to uncontrolled cell division. The transforming activity of ras is dependent upon localization of the protein to plasma membranes. This membrane binding occurs via a series of post-translational modifications of the cytosolic ras proteins. The first and mandatory step in this sequence of events is the farnesylation of these proteins. The reaction is catalyzed by the enzyme farnesyl protein transferase (FPT), and farnesyl pyrophosphate (FPP) serves as the farnesyl group donor in this reaction. The ras C-terminus contains a sequence motif termed a "Cys-Aaa$_1$-Aaa$_2$-Xaa" box (CAAX box), wherein Cys is cysteine, Aaa is an aliphatic amino acid, and Xaa is a serine or methionine. Farnesylation occurs on the cysteinyl residue of the CAAX box (Cys-186), thereby attaching the prenyl group on the protein via a thio-ether linkage.

SUMMARY OF THE INVENTION

The present invention provides compounds of formula I, their enantiomers, diasteromers, tautomers and pharmaceutically acceptable salts, prodrugs and solvates thereof, for use as inhibitors of farnesyl protein transferase and ras protein farnesylation:

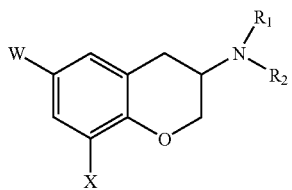

I wherein:
W is hydrogen, halogen, cyano, alkyl, alkynyl, cycloalkyl, heterocyclic, aryl, or heteroaryl;
$R^1$ is alkyl, alkynyl, cycloalkyl, heterocyclic, aryl or heteroaryl;
$R^2$ is $SO_2R^3$, $SO_2NR^4R^5$, $C(=O)NR^6R^7$, or $C(=O)R^8$;
X is $NR^9R^{10}$, $CR^{11}R^{12}R^{13}$;
$R^3$ is alkyl, alkynyl, cycloalkyl, heterocyclic, aryl or heteroaryl; each $R^4$, $R^5$, $R^6$, $R^7$, $R^8$, $R^9$, $R^{10}$ and $R^{14}$ is, independently, hydrogen, alkyl, alkynyl, cycloalkyl, heterocyclic, acyl, aryl or heteroaryl, wherein optionally $R^4$ and $R^5$ together, $R^6$ and $R^7$ together, or $R^9$ and $R^{10}$ together form a heterocycle incorporating the nitrogen atom;
each $R^{11}$, $R^{12}$ and $R^{13}$ is, independently, hydrogen, alkyl, cycloalkyl, heterocyclic, aryl, heteroaryl or $OR^{14}$, wherein $R^{11}$ and $R^{12}$ together optionally form a cycloalkyl attached in a spiro fashion, or a heterocylcoalkyl attached in a spiro fashion, or a carbonyl group (C=O).

The present invention also provides pharmaceutical compositions comprising the compounds of formula I and methods of treating farnesly protein transferase associated disorders using the compounds of formula I.

DETAILED DESCRIPTION OF THE INVENTION

The following are definitions of terms used in the present specification. These definitions apply to the terms as they are used throughout the specification either individually or as part of a larger group, unless otherwise indicated.

The term "alkyl" refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

The "alkyl" may be substituted by one, two, or three substituents. Exemplary substituents include halogen, trifluoromethyl, trifluoromethoxy, alkenyl, alkynyl, nitro, cyano, keto (=O), $OR_a$, $SR_a$, $NR_aR_b$, $NR_aSO_2R_c$, $SO_2R_c$, $SO_2NR_aR_b$, $CO_2R_a$, $C(=O)R_a$, $C(=O)NR_aR_b$, $OC(=O)R_a$, $OC(=O)NR_aR_b$, $NR_aC(=O)R_b$, $NR_aCO_2R_b$, cycloalkyl, heterocyclic, aryl, and heteroaryl, wherein $R_a$ and $R_b$ are selected from hydrogen, alkyl, alkenyl, cycloalkyl, heterocyclic, aryl, and heteroaryl, and $R_c$ is selected from alkyl, alkenyl, cycloalkyl, heterocyclic, aryl and heteroaryl. When a substituted alkyl includes a cycloalkyl, heterocyclic, aryl, or heteroaryl substituent, said ringed systems are as defined below and may optionally be subsituted. When either $R_a$, $R_b$ or $R_c$ is an alkyl or alkenyl, said alkyl or alkenyl may optionally be substituted with 1–3 of halogen, trifluoromethyl, trifluoromethoxy, nitro, cyano, keto (=O), OH, O(alkyl), phenyloxy, benzyloxy, SH, S(alkyl), $NH_2$, NH(alkyl), N(alkyl)$_2$, NHSO$_2$(alkyl), SO$_2$(alkyl), SO$_2$NH$_2$, SO$_2$NH(alkyl), SO$_2$N(alkyl)$_2$, CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, —OC(=O)NH$_2$, —OC(=O)NH(alkyl), NHC(=O)alkyl, and/or NHCO$_2$(alkyl).

"Alkyl" when used in conjunction with another group such as in "arylalkyl" or "cycloalkylalkyl" refers to a substituted alkyl in which at least one of the substituents is the specifically-named group. For example, the term arylalkyl (or aralkyl) includes benzyl, or any other straight or branched chain substituted alkyl having at least one aryl group attached at any point of the alkyl chain.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "cycloalkyl" refers to fully saturated and partially unsaturated hydrocarbon rings of 3 to 9, preferably 3 to 7 carbon atoms, and may be optionally substituted with halogen, alkyl, alkenyl, substituted alkenyl, alkynyl, nitro, cyano, keto (═O), $OR_a$, $SR_a$, $NR_aR_b$, $NR_aSO_2R_c$, $SO_2R_c$, $SO_2NR_aR_b$, $CO_2R_a$, $C(═O)R_a$, $C(═O)NR_aR_b$, $OC(═O)R_a$, $—OC(═O)NR_aR_b$, $NR_aC(═O)R_b$, $NR_aCO_2R_b$, aryl, heteroaryl, heterocyclic, and/or another 4 to 7 membered cycloalkyl ring, wherein $R_a$, $R_b$ and $R_c$ are defined as above. When $R_a$, $R_b$ and $R_c$ are selected from an alkyl or alkenyl group, such groups are in turn optionally substituted as set forth above in the definition for substituted alkyl. The term "cycloalkyl" also includes such rings having a second ring fused thereto (e.g., including benzo, heterocyclic, or heteroaryl rings) or having a carbon-carbon bridge of 3 to 4 carbon atoms. When a cycloalkyl has a second ring fused thereto or is substituted with a further ring, ie., aryl, arylalkyl, heteroaryl, heteroarylalkyl, heterocyclic, heterocyclic, cycloalkylalkyl, or a further cycloalkyl ring, such ring in turn may be substituted with one to two $C_{0-6}$alkyl substituted with one to two of (or bonded to one of) halogen, tirfluoromethyl, $C_{2-6}$alkenyl, nitro, cyano, keto (═O), OH, O(alkyl), phenyloxy, benzyloxy, SH, S(alkyl), $NH_2$, NH(alkyl), $N(alkyl)_2$, $NHSO_2$(alkyl), $SO_2$(alkyl), $SO_2NH_2$, $SO_2NH$(alkyl), $SO_2N(alkyl)_2$, $CO_2H$, $CO_2$(alkyl), C(═O)H, C(═O)alkyl, $C(═O)NH_2$, C(═O)NH(alkyl), $C(═O)N(alkyl)_2$, OC(═O)alkyl, $—OC(═O)NH_2$, —OC(═O)NH(alkyl), NHC(═O)alkyl, and $NHCO_2$(alkyl).

Thus, the term "cycloalkyl" includes cyclopropyl, cyclobutyl, cyclopentyl, cyclohexyl, cycloheptyl, cyclooctyl, etc., as well as the following ring systems,

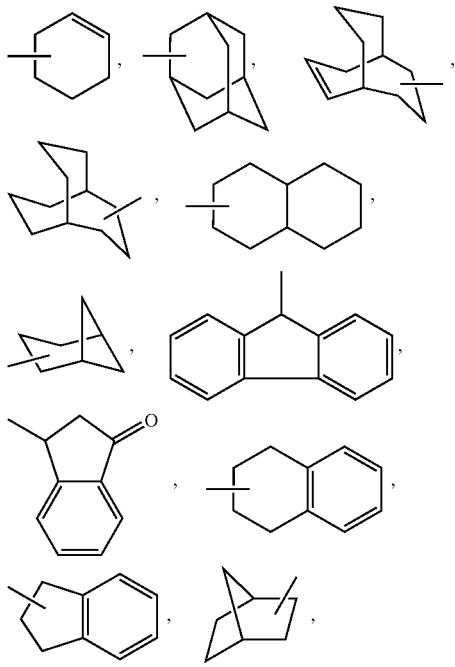

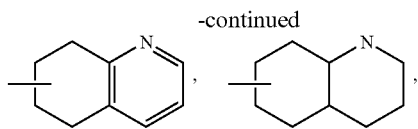

and the like, which optionally may be substituted at any available atoms of the ring(s).

When reference is made to two substituted groups forming a cycloalkyl attached in spiro fashion, it means a fully saturated and partially unsaturated hydrocarbon rings of 3 to 9, preferably 3 to 7 carbon atoms, as in

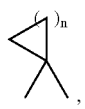

n=1–5, and so forth, which optionally may be substituted with zero to five groups (preferably with zero to two). It may also be fused with one or more rings which is cycloalkyl, heterocylco, or aryl as in:

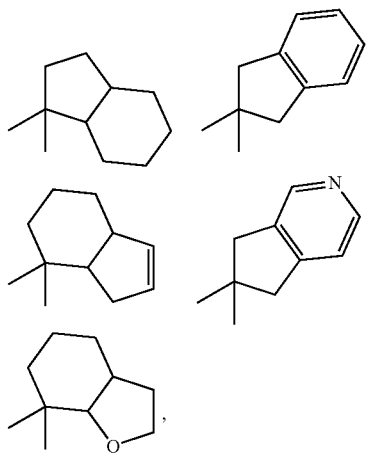

and the like, which optionally may be substituted at any available carbon atom.

The term "acyl" refers to a group having a carbonyl

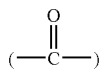

linked to an organic group i.e.,

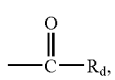

wherein $R_d$ may be selected from alkyl, alkenyl, substituted alkyl, substituted alkenyl, aryl, heterocyclo, cycloalkyl, and heteroaryl, as defined herein.

The term "aryl" refers to phenyl, biphenyl, naphthalenyl, and anthrathenyl, with phenyl being preferred. The term "aryl" includes such rings having zero to three substituents (preferably 0–2 substituents), selected from the group consisting of 1) $R_h$; and 2) $C_{1-6}$ alkyl substituted with one to three $R_g$, wherein $R_g$ is as defined above for cycloalkyl, and $R_h$ is selected from the same groups as $R_g$ but does not include ketone (=O). Additionally, two substituents attached to an aryl, particularly a phenyl group, may join to form a further ring such as a fused or spiro-ring, e.g., cyclopentyl or cyclohexyl, or fused heterocycle or heteroaryl. When an aryl is substituted with a further ring, such ring in turn may be optionally substituted halogen, tirfluoromethyl, $C_{2-6}$alkenyl, nitro, cyano, ketone (=O), OH, O(alkyl), phenyloxy, benzyloxy, SH, S(alkyl), $NH_2$, NH(alkyl), $N(alkyl)_2$, $NHSO_2$(alkyl), $SO_2$(alkyl), $SO_2NH_2$, $SO_2NH$(alkyl), $SO_2N(alkyl)_2$, $CO_2H$, $CO_2$(alkyl), C(=O)H, C(=O)alkyl, $C(=O)NH_2$, C(=O)NH(alkyl), $C(=O)N(alkyl)_2$, OC(=O)alkyl, $—OC(=O)NH_2$, —OC(=O)NH(alkyl), NHC(=O)alkyl, and $NRCO_2$(alkyl).

Thus, examples of aryl groups include:

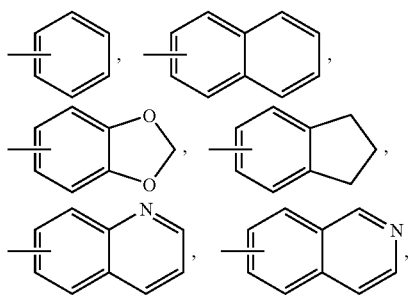

and the like, which optionally may be substituted at any available carbon or nitrogen atom.

The term "heterocycle" or "heterocyclic" refer to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclic group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain nitrogen and carbon atoms, where the carbon atoms may be saturated, partially saturated, or unsaturated. The nitrogen and sulfur atoms may optionally be oxidized and the nitrogen atoms may optionally be quaternized. The heterocyclic group may be attached at any available nitrogen or carbon atom. The heterocyclic ring may be optionally substituted. Exemplary substituents include $C_1$ to $C_6$ alkyl, halogen, trifluoromethyl, $C_{2-6}$alkenyl, nitro, cyano, keto (=O), OH, O(alkyl), phenyloxy, benzyloxy, SH, S(alkyl), $NH_2$, NH(alkyl), $N(alkyl)_2$, $NHSO_2$(alkyl), $SO_2$(alkyl), $SO_2NH_2$, $SO_2NH$(alkyl), $SO_2N(alkyl)_2$, $CO_2H$, $CO_2$(alkyl), C(=O)H, C(=O)alkyl, $C(=O)NH_2$, C(=O)NH(alkyl), $C(=O)N(alkyl)_2$, OC(=O)alkyl, $—OC(=O)NR_2$, —OC(=O)NH(alkyl), NHC(=O)alkyl, and $NHCO_2$(alkyl).

Exemplary heterocyclic groups include, without limitation:

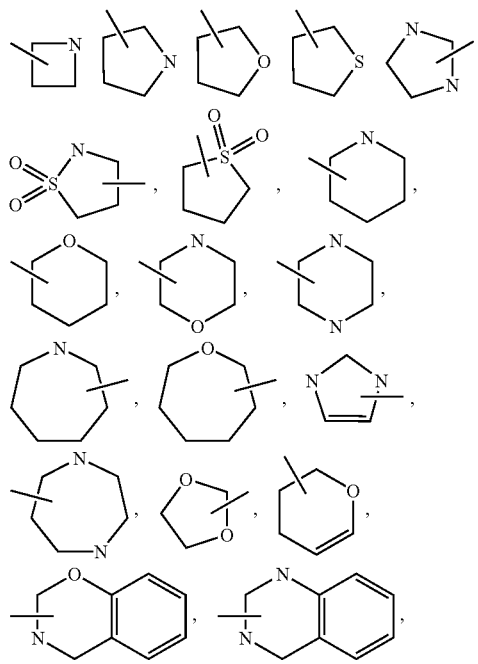

and the like, which optionally may be substituted at any available carbon or nitrogen atom.

When reference is made to two substituted groups forming a heterocyclic attached in Spiro fashion, exemplary examples include:

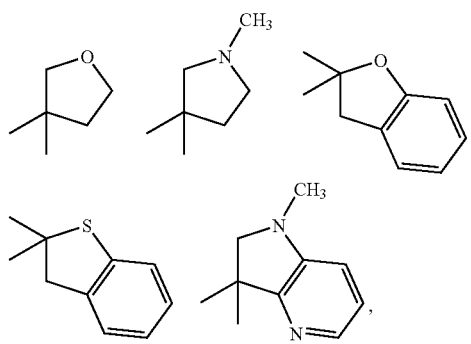

and so forth, which optionally may be substituted at any available carbon or nitrogen atom.

The term "heteroaryl" refers to substituted and unsubstituted aromatic 5 to 7 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain nitrogen and carbon atoms, where the carbon atoms may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be optionally substituted with $C_1$ to $C_6$ alkyl, halogen, trifluoromethyl, $C_{2-6}$alkenyl, nitro, cyano, keto (=O), OH, O(alkyl), phenyloxy, benzyloxy, SH, S(alkyl), $NH_2$, NH(alkyl), N(alkyl)$_2$, $NHSO_2$(alkyl), $So_2$(alkyl), $SO_2NH_2$, $SO_2NH$(alkyl), $SO_2N$(alkyl)$_2$, $CO_2H$, $CO_2$(alkyl), C(=O)H, C(=O)alkyl, C(=O)$NH_2$, C(=O)NH(alkyl), C(=O)N(alkyl)$_2$, OC(=O)alkyl, —OC(=O)$NH_2$, —OC(=O)NH(alkyl), NHC(=O)alkyl, and $NHCO_2$(alkyl).

Examples of heteroaryl rings include

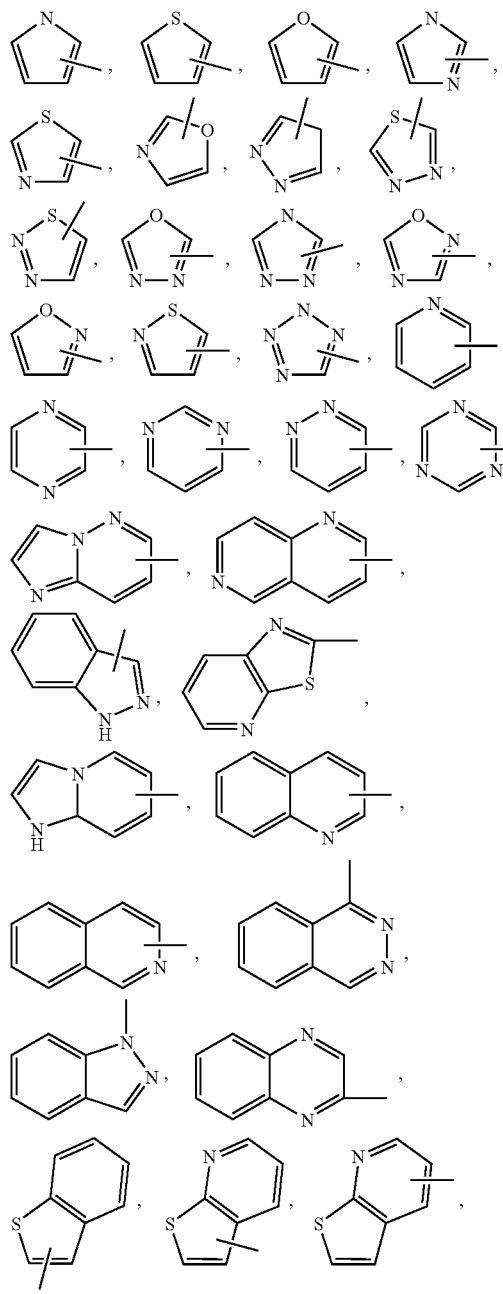

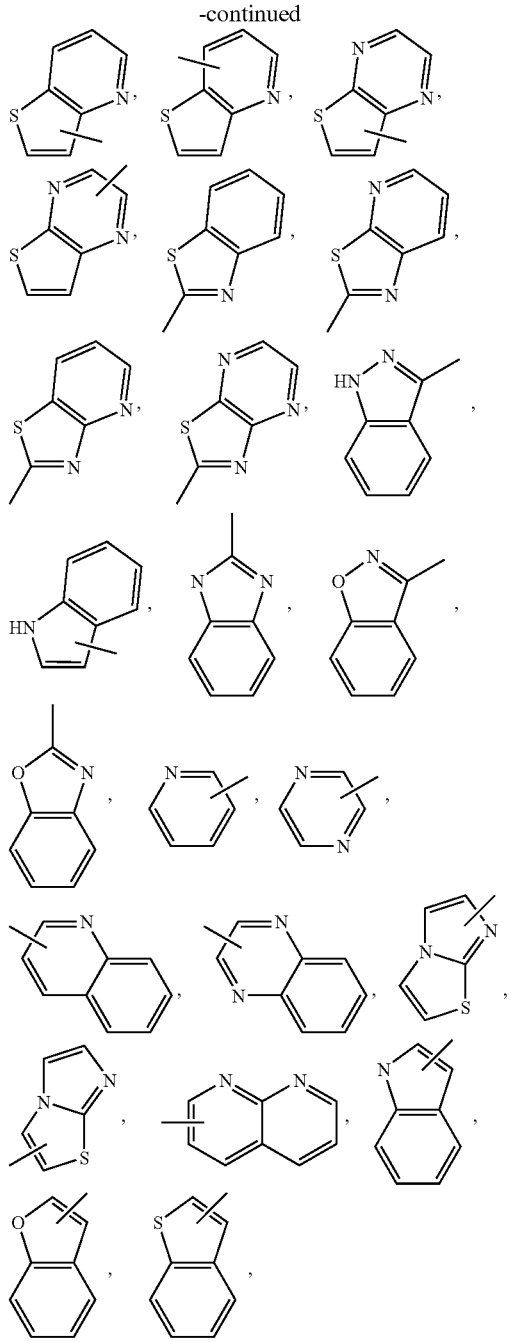

and the like, which optionally may be substituted at any available carbon or nitrogen atom.

When the term "unsaturated" is used herein to refer to a ring or group, the ring or group may be fully unsaturated or partially unsaturated.

It should be understood that one skilled in the field may make various substitutions for each of the groups recited in the claims herein, without departing from the spirit or scope of the invention.

Throughout the specification, groups and substituents thereof may be chosen by one skilled in the field to provide stable moieties and compounds.

The compounds of formula I form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula I contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard,p. 113–191 (1991); and c) H. Bundgaard, *Advanced Drug Delivery Reviews*, 8, 1–38 (1992), each of which is incorporated herein by reference.

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Compounds of formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

The compounds of the instant invention may, for example, be in the free or hydrate form, and may be obtained by methods herein.

As described above, the present invention encompasses compounds of the following formula I, and salts thereof, for use as farnesyl protein transferase inhibitors:

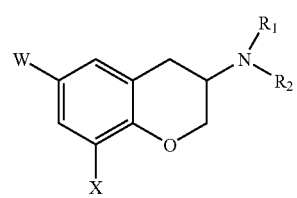

wherein:
W is hydrogen, halogen, cyano, alkyl, alkynyl, cycloalkyl, heterocyclic, aryl, or heteroaryl;
$R^1$ is alkyl, alkynyl, cycloalkyl, heterocyclic, aryl or heteroaryl;
$R^2$ is $SO_2R^3$, $SO_2NR^4R^5$, $C(=O)NR^6R^7$, or $C(=O)R^8$;
X is $NR^9R^{10}$, $CR^{11}R^{12}R^{13}$;
$R^3$ is alkyl, alkynyl, cycloalkyl, heterocyclic, aryl or heteroaryl;
each $R^4$, $R^5$, $R^6$, $R^7$, $R^8$, $R^9$, $R_{10}$ and $R^{14}$ is, independently, hydrogen, alkyl, alkynyl, cycloalkyl, heterocyclic, acyl, aryl or heteroaryl, wherein optionally $R^4$ and $R^5$ together, $R^6$ and $R^7$ together, or $R^9$ and $R^{10}$ together form a heterocycle incorporating the nitrogen atom;
each $R^{11}$, $R^{12}$ and $R^{13}$ is, independently, hydrogen, alkyl, cycloalkyl, heterocyclic, aryl, heteroaryl or $OR^{14}$, wherein $R^{11}$ and $R^{12}$ together optionally form a cycloalkyl attached in a spiro fashion, or a heterocylcoalkyl attached in a spiro fashion, or a carbonyl group (C=O).

Preferred compounds of the present invention are compounds of the formula I, and salts thereof, wherein:
W is hydrogen, halogen, cyano;
$R^1$ is alkyl, aryl or heteroaryl;
and all other constituents are as previously described.

More preferred compounds of the present invention are compounds of the formula I, and salts thereof, wherein:
W is cyano;
$R^1$ is benzyl or thiophenyl;
and all other constituents are as previously described.

Use and Utility

The compounds of formulas I are inhibitors of S-farnesyl protein transferase. They are thus useful in the treatment of a variety of cancers, including (but not limited to) the following:
carcinoma, including that of the bladder, breast, colon, kidney, liver, lung, ovary, pancreas, stomach, cervix, thyroid and skin; including squamous cell carcinoma;
hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;
hematopoietic tumors of myeloid lineage, including acute and chronic myelogenous leukemias and promyelocytic leukemia;
tumors of mesenchymal origin, including fibrosarcoma and rhabdomyoscarcoma;
other tumors, including melanoma, seminoma, tetratocarcinoma, neuroblastoma and glioma;
tumors of the central and peripheral nervous system, including astrocytoma, neuroblastoma, glioma, and schwannomas;
tumors of mesenchymal origin, including fibrosarcoma, rhabdomyoscaroma, and osteosarcoma; and
other tumors, including melanoma, xenoderma pigmentosum, keratoactanthoma, seminoma, thyroid follicular cancer and teratocarcinoma.

The compounds of formulas I are especially useful in treatment of tumors having a high incidence of ras involvement, such as colon, lung, and pancreatic tumors. By the administration of a composition having one (or a combination) of the compounds of this invention, development of tumors in a mammalian host is reduced.

Compounds of formulas I are also useful in the treatment of diseases other than cancer that are associated with signal transduction pathways operating through ras, e.g., neurofibromatosis, atherosclerosis, pulmonary fibrosis, arthritis, psoriasis, glomerulonephritis, restenosis following angioplasty or vascular surgery, hypertrophic scar formation and endotoxic shock. Compounds of formulas I are also useful as anti-fungal agents.

Compounds of formulas I are also useful in the treatment of diseases associated with farnesyl transferase substrates other than ras (e.g., nuclear lamins and transducin) that are also post-translationally modified by the enzyme farnesyl protein transferase.

Compounds of formulas I also act as inhibitors of other prenyl transferases (e.g., geranylgeranyl transferase I), and thus can be effective in the treatment of diseases associated with other prenyl modifications (e.g., geranylgeranylation) of proteins (e.g. the rap, rab, rac and rho gene products and the like). For example, they may find use as drugs against Hepatitis delta virus (HDV) infections, as suggested by the recent finding that geranylgeranylation of the large isoform of the delta antigen of HDV is a requirement for productive viral infection [J. S. Glen, et al., *Science*, 256, 1331 (1992)].

Compounds of formula I also induce or inhibit apoptosis, a physiological cell death process critical for normal development and homeostasis. Alterations of apoptotic pathways contribute to the pathogenesis of a variety of human diseases. Compounds of formula I, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpesvirus, poxvirus, Epstein-Barr virus, Sindbis virus and adenovirus), autoimmune diseases (including but not limited to systemic lupus erythematosus, immune mediated glomerulonephritis, rheumatoid arthritis, psoriasis, inflammatory bowel diseases and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

The compounds of this invention are also useful in combination with known anti-cancer and cytotoxic agents i.e. Topoisomerase I and II inhibitors, antimetabolites, agents that affect microtubules, DNA intercalaters and binders, agents that interfere with angiogenesis, DNA alkylating agents, hormonal agents, protein kinase inhibitors, ribonucleotide reductase inhibitors, mitochondrial respiratory inhibitors, agents that affect Golgi apparatus, telomerase inhibitors, prenyl transferase inhibitors, cell membrane interactive agents, and treatments, including radiation. If formulated as a fixed dose, such combination products employ the compounds of this invention within the dosage range described below and the other pharmaceutically active agent within its approved dosage range. Compounds of formulas I can be used sequentially with known anticancer or cytotoxic agents and treatment, including radiation when a combination formulation is inappropriate.

Farnesyl transferase assays were performed as described in V. Manne et al., *Drug Development Research*, 34, 121–137, (1995). The compounds of the present invention are inhibitors of farnesyl transferase with IC 50 values between 1nM and 100 uM.

The compounds of this invention can be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds are administered in a dosage range of about 0.05 to 200 mg/kg/day, preferably less than 100 mg/kg/day, in a single dose or in 2 to 4 divided doses.

Methods of Preparation

Compounds of formula I may be prepared according to the following Schemes. Solvents, temperatures, pressures, and other reaction conditions may readily be selected by the knowledge of one skilled in the art.

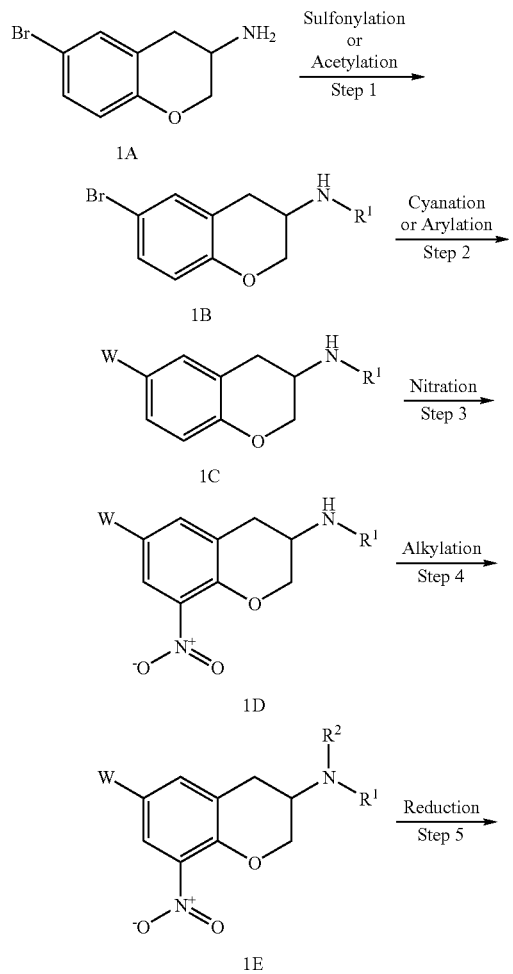

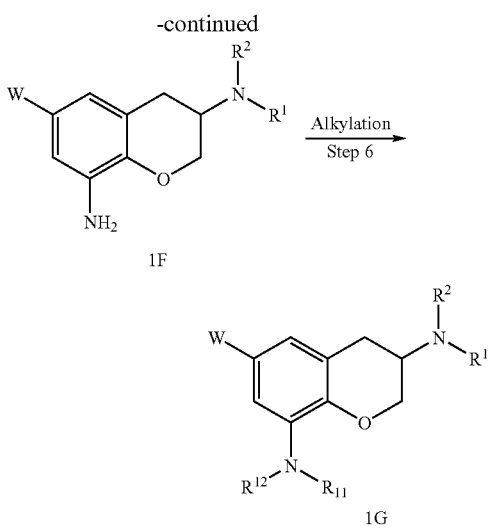

Compound 1A could be obtained by someone skilled in the art by following the published procedure (Eur. J. Med. Chem. 497, 26, 1991).

In step 1, compound 1A can be converted to the corresponding sulfonamide 1B by reacting with a sulfonylation reagent, e.g., methane sulfonyl chloride.

In step 2, the halogen group (e.g., Br) of compound 1B can be converted to other groups, for example, cyano, aryl, or heteroaryl by reacting with an appropriate reagent in the presence of a catalyst like palladium.

In step 3, compound 1C can be regiospecifically nitrated to give compound 1D.

In step 4, compound 1D can undergo alkylation on nitrogen, for example, with benzyl chloride in the presence of a base such as sodium hydride to give compound 1E.

In step 5, the nitro group of compound 1E can be reduced by a reducing agent such as hydrogen over palladium catalyst.

In step 6, compound 1F can be alkylated at the free aniline group under reductive amination condition, e.g., reacting with imidazole carboxaldehyde in the presence of triethyl silane to give compound 1G.

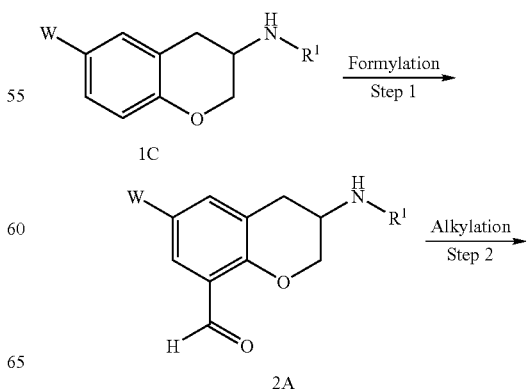

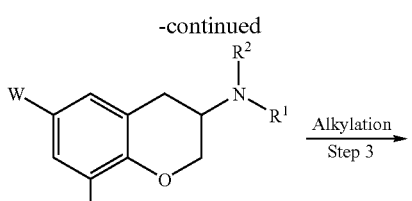

2B

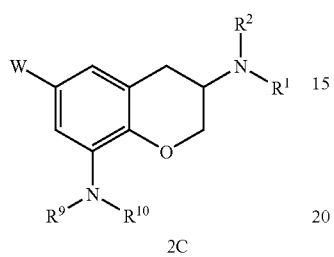

2C

In step 1 of Scheme 2, compound 1C can be converted to compound 2A through formylation reaction such as treatment with α,α-dichloromethyl methyl ether in the presence of a Lewis acid such as titanium tetrachloride.

In step 2 of Scheme 2, compound 2A can be converted to compound 2B by treatment with an alkylating agent such as benzyl bromide in the presence of a base such as cesium carbonate.

In step 3 of Scheme 2, compound 2B can be converted to compound 2C by treatment with a Grignard agent such as imidazole magnesium bromide.

In addition, other compounds of formula I may be prepared using procedures generally known to those skilled in the art. In particular, the following examples provide additional methods for preparing compounds of this invention. These examples are illustrative rather than limiting, and it is to be understood that there may be other embodiments that fall within the spirit and scope of the invention as defined by the claims appended hereto.

Conditions

All temperatures are in degrees Celsius (° C.) unless otherwise indicated. Reverse phase (RP) HPLC purifications were done by eluting with a mixture of methanol in water containing 0.1% TFA on. YMC S5 ODS 4.6×50 mm column over 4 min, 4 mL/min. The retention times are reported as Rt. All the synthesized compounds were characterized by at least proton NMR and LC/MS. During work up of reactions, the organic extract was dried over Magnesium sulfate (MgSO$_4$), unless mentioned otherwise.

ABBREVIATIONS

NMM=N-methylmorpholine;
DIBALH=diisobutylaluminum hydride;
BOP reagent=benzotriazol-1-yloxy-tris(trimethylamino) phosphonium hexafluorophosphate;
DCE=dichloroethane;
DCC=dicyclohexyl carbodiimide;
EDCI=1-(dimethylaminopropyl)-3-ethylcabodiimide hydrochloride;
HOBt=hydroxybenzotriazole;
DCM=dichloromethane;
CbzCl=chlorobenzoyl chloride;
TFA=trifluoroacetic acid;
DIPEA=diisopropylamine.

EXAMPLE 1

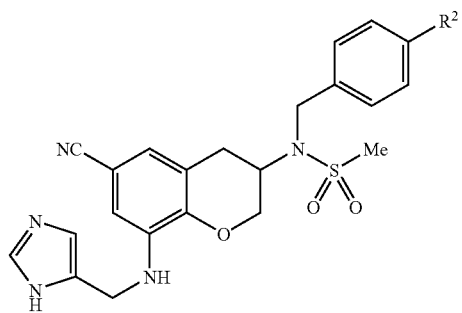

N-Benzyl-N-[6-cyano-8-(3H-imidazol-4-ylamino)-chroman-3-yl]-methanesulfonamide

A) A mixture of 5-bromosalicyldehyde (8.04 g, 40 mmoles), nitroethanol (7.28 g, 80 mmol) and dibutylamine hydrocholoride (3.28 g, 20 mmol) in isoamylacetate (80 mL) was heated to reflux with Dean-Stark trap (see Eur. J. Med. Chem. 497, 26, 1991). After 2 h, the reaction mixture was cooled to RT and concentrated in vacuo. The residue was purified by flash column chromatography eluting with hexanes in dichloromethane (2:1) to afford a yellow solid which was dissolved in dichloromethane and washed with 1 N NaOH (3 times). The organic layer was dried, and concentrated to afford 6-bromo-3-nitro-2H-chromene (4.0 g, 39%) as an yellow solid.

B) To a solution of compound 1A (4.0 g, 15.6 mmol) in chloroform (100 mL) and isopropanol (40 mL) was added silica gel (10 g, 230 Mesh), followed by sodium borohydride (1.5 g, 39.7 mmol) in small portions. After stirring for 20 min, acetic acid (1.5 mL) was added dropwise. After 20 min, the reaction mixture was filtered and the filtrate was concentrated to afford a white solid. The residue was purified by flash column chromatography to afford 6-bromo-3-nitro-chroman (3.6 g, 89%) as a solid.

C) To a stirring mixture of compound 1B (2.58 g, 10 mmol) and Raney Nickel (2 g) in ethanol (100 mL) at 45° C. was added hydrazine (5 mL, 40% in tetrahydrofuran) dropwise over 0.5 h. After 30 min more, the mixture was cooled to RT, filtered through a pad of celite, and the filtrate was concentrated in vacuo. The residue was purified by flash column chromatography eluting with 2% methanol in dichloromethane containing 0.1% ammonia to afford 6-bromo-chroman-3-ylamine (2.1 g, 89%) as an oil. LC/MS; (M+H)$^+$=228.2.

D) Compound 1C (77.7 g, 0.29 M) was mixed with ethyl acetate (25 mL), NaHCO$_3$ (2 g) in water (5 mL), and methanesulfonyl chloride (1.17 g, 10.2 mmol). The mixture was stirred for 1 h, and then the two layers were separated and the aqueous layer was extracted with ethyl acetate. The organic layer was dried, and concentrated to afford a solid which was further purified by trituration with diethyl ether to afford N-(6-bromo-chroman-3-yl)-methanesulfonamide (21.15 g, 83%) as white solid. LC/MS; (M+H)$^+$=304.3, 306.2.

E) To a solution of compound 1D (918 mg, 3 mmol) in NMP (10 mL) was added cuprous cyanide (918 mg, 10.3 mmol) and the resulting mixture was heated at 195° C. After 6 h, the mixture was cooled to RT and water (30 mL) was added. The precipitate formed was washed with water and the solid was extracted with 10% methanol in dichloromethane. The combined extracts were concentrated to afford the desired product, N-(6-cyano-chroman-3-yl)-methanesulfonamide (610 mg, 80%) as a white solid. LC/MS; (M+H)$^+$=253.3.

F) To a solution of compound 1E (252 mg, 1 mmol) in chloroform (15 mL) were added KNO$_3$ (150 mg, 1.49 mmol) and TFA anhydride (0.5 mL, 3.5 mmol). After stirring at RT for 3 h, the mixture was washed with saturated NaHCO$_3$ solution. The organic layer was separated and the aqueous layer was extracted with dichloromethane. The combined organic layer was dried, concentrated and the residue was purified by flash column chromatography eluting with 2% methanol in dichloromethane to afford N-(6-cyano-8-nitro-chroman-3-yl)-methanesulfonamide (120 mg, 40%).

G) A mixture of compound 1F (150 mg, 0.5 mmol), benzyl alcohol (270 mg, 2.5 mmol), triphenylphosphine (655 mg, 2.5 mmol), and DIALD (505 mg, 2.5 mmol) in tetrahydrofuran (3 mL) was stirred at 50° C. for 2 h. The mixture was then cooled to RT, concentrated and the resulting residue was purified by silica gel column chromatography using ethyl acetate/hexanes (1:2) to afford N-benzyl-N-(6-cyano-8-nitro-chroman-3-yl)-methanesulfonamide (170 mg, 88%). LC/MS; (M+H)$^+$=388.4.

H) To a solution of compound 1G (160 mg, 0.41 mmol) in ethyl acetate (15 mL) was added 10% Pd/C (60 mg) and the resulting mixture was stirred under hydrogen (balloon) for 5 h. It was then filtered, concentrated and the residue was purified by silica gel column chromatography using ethyl acetate/hexanes (1:1)to afford N-(8-amino-6-cyano-chroman-3-yl)- N-benzyl methanesulfonamide (120 mg, 82%). LC/MS; (M+H)$^+$=358.2.

I) A mixture of 1H (100 mg, 0.28 mmol), 4-imidazolecarboxaldehyde (31.6 mg, 0.33 mmol), and TFA (0.2 mL) in dichloromethane (2 mL) was stirred at RT for 10 min. Triethylsilane (0.1 mL) was added dropwise to the above mixture. After 1 h, aqueous NaHCO$_3$ and dichloromethane were added to the reaction mixture. The organic layer was separated, dried and concentrated. The residue was purified by silica gel column chromatography using ethyl acetate/ hexanes (1:1) to afford the title compound (120 mg, 100%). LC/MS; (M+H)$^+$=438. RP HPLC Rt=2.77 min. (YMC S5 ODS 4.6×50 mm, 10%-90% aqueous methanol containing 0.1% TFA over 4 min, 4 mL/min).

EXAMPLE 2

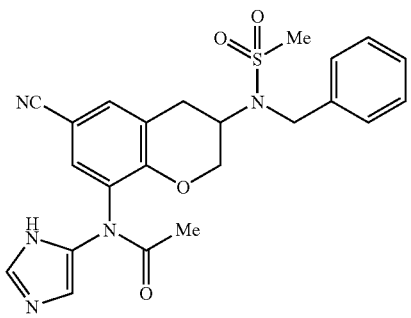

N-[3-(Benzyl methanesulfonylamino)-6-cyanochroman-8-yl]-N-(3H-imidazol-4-yl)acetamide A solution of Example 1 (20 mg, 0.046 mmol ) in acetic anhydride (0.1 mL) was stirred at RT. After 3 h, methanol was added to the mixture. After stirring for 16 h, the mixture was neutralized with aqueous NaHCO$_3$ and extracted with dichloromethane. The combined extract was dried, and concentrated in vacuo. The residue was dissolved in methanol, HCl (1N, 0.05 mL)) and water (2 mL). After 20 min, the mixture was concentrated to remove methanol and the remaining residue was lyophilized to afford the title compound (12 mg, 50%) as a hydrochloride salt. LC/MS; (M+H)$^+$=480.7. RP HPLC Rt=2.56 min.

EXAMPLE 3

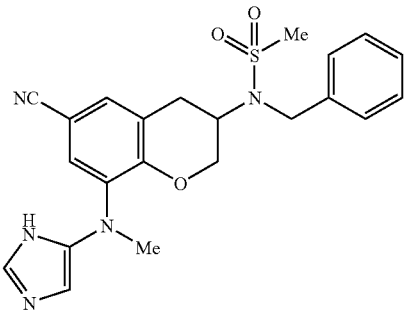

N-Benzyl-N-{6-cyano-8-[(3H-imidazol-4-yl)-methyl-amino]-chroman-3-yl}-methanesulfonamide To a solution of Example 1 (20 mg, 0.049 mmol) in dichloromethane (1 mL) paraformaldehyde (50 mg), TFA (0.1 mL) and triethylsilane (0.1 mL) were added. After stirring at RT for 2 h, and the mixture was neutralized with aqueous NaHCO$_3$ solution, the organic layer was separated and the aqueous layer was extracted with dichloromethane (2 times). The combined organic layer was dried, filtered and concentrated. The residue was purified by SCX® cartridge eluting with methanol and then with 2N ammonia in methanol. The fractions containing desired product were treated with a solution containing 1N HCl (0.05 mL) and water (2 mL) and lyophilized to afford the title compound as a hydrochloride salt (12 mg, 65%), a white solid. MS: (M+H)$^+$=451. RP HPLC Rt=2.77 min.

EXAMPLE 4

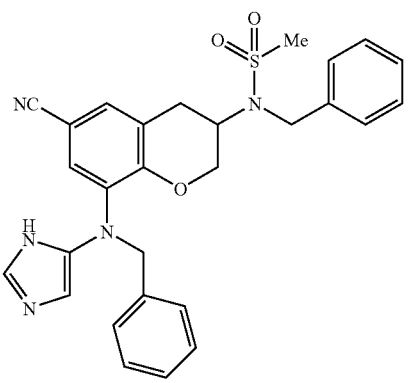

N-Benzyl-N-{8-[benzyl-(3H-imidazol-4-yl)-amino]-6-cyano-chroman-3-yl}-methanesulfonamide The procedure described for the preparation of Example 3 was followed to convert Example 1 (22 g, 0.5 mmol) by treatement with benzaldehyde (0.1 mL) to the title compound (4 mg, 20%) as HCl salt. LC/MS; (M+H)⁺=528.3. HPLC Rt=3.36 min.

EXAMPLE 5

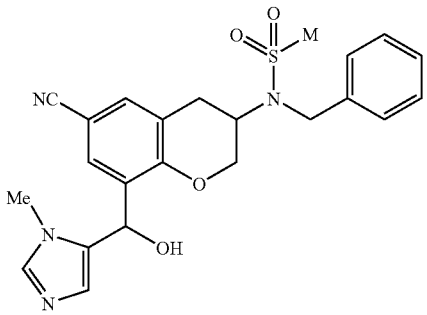

N-Benzyl-N-{6-cyano-8-[hydroxy-(3-methyl-3H-imidazol-4-yl)-methyl]-chroman-3-yl}-methanesulfonamide A) To a solution of compound 1D of Example 1 (306 mg, 1.0 mmol) in dichloromethane (10 mL) were added TiCl$_4$ in dichloromethane (1M, 2.5 mL, 2.5 mmol) and α,α-dichloromethyl methyl ether (0.5 mL). After stirring at RT overnight, water (2 mL) was added and the mixture was refluxed for 3 h. After cooling to RT, the organic layer was separated, dried and concentrated in vacuo. The resulting residue was triturated with ether and dried in vacuo to afford N-(6-bromo-8-formyl-chroman-3-yl)-methanesulfonamide (230 mg, 69%).

B) To a solution of compound 5A (334 mg, 1 mmol) in dimethyl formamide (3 mL) were added Cs$_2$CO$_3$ (650 mg, 2 mmol) and benzyl bromide (256 mg, 1.5 mmol) and the mixture was stirred at RT for 2 h. The mixture was washed with water (10 mL) and extracted with dichloromethane (3 times). The combined organic extracts were dried, concentrated and the residue was purified by flash silica gel column chromatography eluting with 2% methanol in dichloromethane to afford N-benzyl-N-(6-bromo-8-formyl-chroman-3-yl)-methanesulfonamide (360 mg, 85%).

C) To a solution of compound 5B (360 mg, 0.85 mmol) in dimethyl formamide (4 mL) were added zinc cyanide (200 mg, 1.7 mmol), and Pd(Ph$_3$)$_4$ (100 mg, 0.09 mmol). After stirring for 3 h at 90° C. under Argon, the mixture was cooled to RT and diluted with dichloromethane (20 mL) and filtered through a pad of Celite®. The filtrate was concentrated and the residue was purified by flash silica gel column chromatography eluting with ethyl acetate in hexanes (1:1) to afford N-benzyl-N-(6-cyano-8-formyl-chroman-3-yl)-methanesulfonamide (280 mg, 89%).

D) To a solution of 1-methyl-5-iodoimidazole (208 mg, 1 mmol) in dichloromethane (10 mL) under Argon was added a solution of ethyl magnesium bromide (3M in ether, 0.4 mL, 1.2 mmol). The resulting solution was stirred at RT for 1.5 h, then a solution of compound 5C (185 mg, 0.5 mmol) in dichloromethane (5 mL) was added. After stirring at RT overnight, the mixture was treated with saturated NH$_4$Cl solution and the organic layer was separated, dried and concentrated. The residue was purified by flash silica gel column to afford the title compound(165 mg, 73%) as a mixture of diastereomers.

E) The above mixture of diastereomers was separated by preparative RP HPLC eluting with a mixture of methanol in water containing 0.1% TFA, then converted to respective HCl salts.

Isomer A: HPLC RT=2.37 min, LC/MS; (M+H)⁺=453.

Isomer B: HPLC RT=2.52 min. LC/MS; (M+H)⁺=453.

EXAMPLE 6

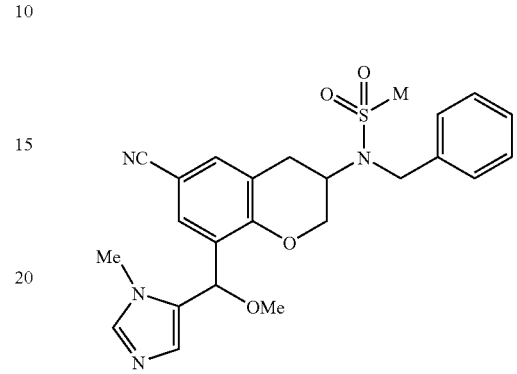

N-Benzyl-N-{6-cyano-8-[methoxy-(3-methyl-3H-imidazol-4-yl)-methyl]-chroman-3-yl}-methanesulfonamide Sodium hydride (60% in oil, 3.3 mg, 0.08 mmol) was washed with hexanes, and then suspended in dimethyl formamide. To this suspension, a solution of compound 5D (25 mg, 0.55 mmol) in dimethyl formamide (0.5 mL) was added. After 10 min at RT, the mixture was cooled to 0° C., and iodomethane (15 mg, 0.11 mmol) was added. After 2 h, one drop was acetic acid was added and the resulting mixture was purified by preparative HPLC to obtain two isomers which were converted to the HCl salt and lyophilized.

Isomer I (5.5 mg): LC/MS; (M+H)⁺=467. HPLC Rt=2.58 min.

Isomer II (8.0 mg): LC/MS; (M+H)⁺=467. HPLC Rt=2.76 min.

EXAMPLE 7

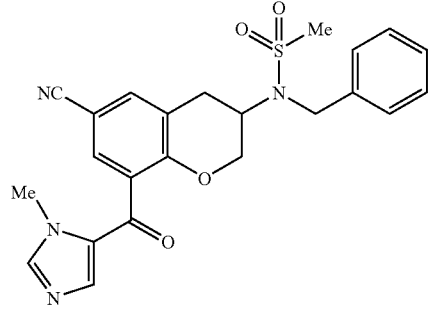

N-Benzyl-N-[6-cyano-8-(3-methyl-3H-imidazole-4-carbonyl)-chroman-3-yl]-methanesulfonamide To a solution of Example 5 (45 mg, 0.1 mmol) in dichloromethane (3 mL) at RT was added Dess-Martin reagent (102 mg) and the mixture was stirred at RT overnight. The mixture was diluted with dichloromethane and washed with 1N NaOH solution. The combined organic extracts were dried, concentrated and the residue was purified by flash silica gel column chromatography followed by RP HPLC. The desired fractions were concentrated and the residue was converted to HCl salt and lyophilized to afford the title compound (39 mg, 86%) as a solid. MS: (M+H)$^+$= 451. HPLC RT=2.84 min.

EXAMPLE 8

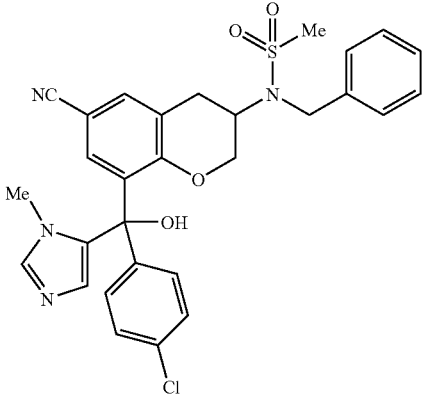

N-Benzyl-N-{8-[(4-chloro-phenyl)-hydroxy-(3-methyl-3H-imidazol-4-yl)-methyl]-6-cyano-chroman-3-yl}-methanesulfonamide To suspension of Example 7 (25 mg, 0.5 mmol) in tetrahydrofuran (0.5 mL) at 0° C. was added a solution of p-chlorophenyl magnesium bromide (1M in ether, 0.1 mL, 0.1 mmol). After stirring for 2 h at RT, the mixture was treated with NH$_4$Cl solution and extracted with dichloromethane. The combined organic extracts were dried, concentrated and the residue was purified by reverse phase preparative HPLC. The appropriate fraction were mixed, concentrated and converted to HCl salt to afford the title compound (25 mg, 87%). LC/MS: (M+H)$^+$=561, 563 (3:1 ratio).

EXAMPLE 9

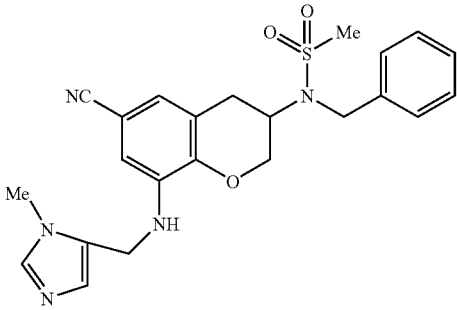

N-Benzyl-N-{6-cyano-8-[(3-methyl-3H-imidazol-4-ylmethyl)-amino]-chroman-3-yl}-methanesulfonamide Compound 1H of Example 1 (50 mg, 0.14 mmol) was treated with 1-methyl-5-imidazolecarboxaldehyde (23 mg, 0.21 mmol) in a manner similar to the preparation of Example 1 (procedure I) to afford the title compound (60 mg, 85%). MS (ESI): (M+H)$^+$=452. HPLC RT=2.68 min.

EXAMPLE 10

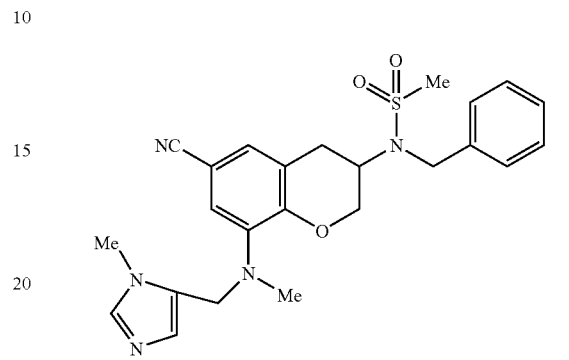

N-Benzyl-N-{6-cyano-8-[methyl-(3-methyl-3H-imidazol-4-ylmethyl)-amino]-chroman-3-yl}-methanesulfonamide Example 9 (49 mg, 0.1 mmol), was converted to the title compound (7.5 mg, 14%) as the HCl salt in a manner similar to the preparation of Example 3. LC/MS; (M+H)$^+$=466.2. HPLC RT=2.72 min.

EXAMPLE 11

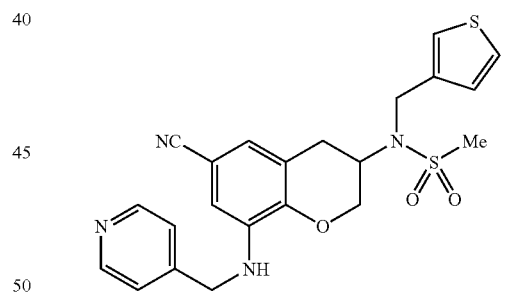

N-{6-Cyano-8-[(pyridin-4-ylmethyl)-amino]-chroman-3-yl}-N-thiophen-3-ylmethyl-methanesulfonamide A) Compound 1F was converted to N-(6-cyano-8-nitro-chroman-3-yl)-N-thiophene-3-ylmethyl-methanesulfonamide (40%) by treatment with 3-thiophenemethanol in a manner similar to the preparation of compound 1G. LC/MS; (M+H)$^+$=394.3.

B) Compound 11A was converted to the title compound in a manner similar to the conversion of compound 1G to Example 1 except pyridine-4-carboxaldehyde was used in the second step. LC/MS; (M+H)$^+$=469.5.

EXAMPLE 12

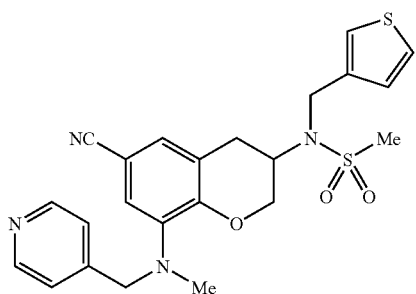

N-[6-Cyano-8-(methyl-pyridin-4-ylmethyl-amino)-chroman-3-yl]-N-thiophen-3-ylmethyl-methanesulfonamide Example 11 (89 mg, 0.2 mmol) was converted to the title compound (31 mg) in a manner similar to the preparation of Example 3. LC/MS; (M+H)$^+$=469.5.

EXAMPLE 13

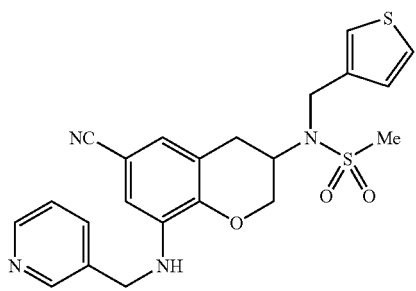

N-{6-Cyano-8-[(pyridin-3-ylmethyl)-amino]-chroman-3-yl}-N-thiophen-3-ylmethyl-methanesulfonamide Compound 11A was converted to the title compound in a manner similar to the conversion of compound 1G to Example 1 except pyridine-3-carboxaldehyde was used in the second step. LC/MS; (M+H)$^+$=469.5.

EXAMPLE 14

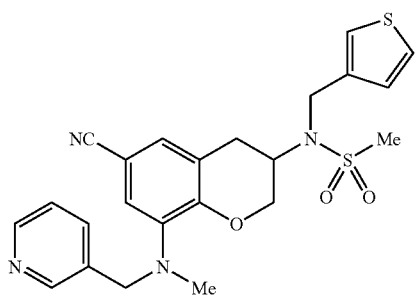

N-[6-Cyano-8-(methyl-pyridin-3-ylmethyl-amino)-chroman-3-yl]-N-thiophen-3-ylmethyl-methanesulfonamide Example 12 (164 mg, 0.36 mmol) was converted to the title compound (127 mg, 76%) in a manner similar to the preparation of Example 3. LC/MS; (M+H)$^+$=469.5.

EXAMPLE 15

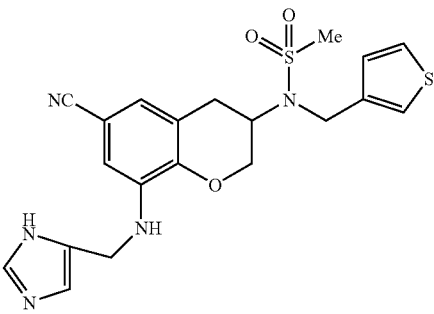

N-{6-Cyano-8-[(3H-imidazol-4-ylmethyl)-amino]-chroman-3-yl}-N-thiophen-3-ylmethyl-methanesulfonamide The title compound (122 mg) was prepared from compound 1G in a manner similar to the preparation of Example 1. LC/MS; (M+H)$^+$=444.4.

What is claimed is:

1. A compound of formula (I):

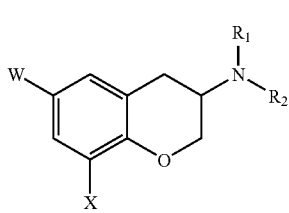

or a pharmaceutically acceptable salt thereof wherein:
W is halogen, cyano, alkyl, alkynyl, cycloalkyl, heterocyclic, aryl, or heteroaryl;
$R^1$ is alkyl, alkynyl, cycloalkyl, heterocyclic, aralkyl, heteroaryl or heteroarylalkyl;
$R^2$ is $SO_2R^3$, $SO_2NR^4R^5$, $C(=O)NR^6R^7$, or $C(=O)R^8$;
X is $NR^9R^{10}$ or $CR^{11}R^{12}R^{13}$;
$R^3$ is alkyl, alkynyl, cycloalkyl, heterocyclic, aryl or heteroaryl;
$R^4$, $R^5$, $R^6$, $R^7$, $R^8$, $R^9$, $R^{10}$ and $R^{14}$ are each, independently, hydrogen, alkyl, alkynyl, cycloalkyl, heterocyclic, acyl, aryl, heteroaryl or heteroarylalkyl, wherein optionally $R^4$ and $R^5$ together, $R^6$ and $R^7$ together, or $R^9$ and $R^{10}$ together form a heterocycle incorporating the nitrogen atom;
$R^{11}$, $R^{12}$ and $R^{13}$ are independently, hydrogen, alkyl, cycloalkyl, heterocyclic, aryl, heteroaryl or $OR^{14}$, wherein $R^{11}$ and $R^{12}$ together optionally form a cycloalkyl attached in a spiro fashion, or a heterocylcoalkyl attached in a spiro fashion, or a carbonyl group (C=O).

2. The compound according to claim 1 wherein W is CN and $R^1$ is arylalkyl or heteroaryl.

3. The compound according to claim 1 wherein $R^1$ is a benzyl or thiophenyl.

4. The compound according to claim 1 wherein X is $-NR^9R^{10}$ and $R^9$ is H, alkyl, aralkyl or acyl and $R^{10}$ is heteroaryl or heteroarylalkyl.

5. The compound according to claim 4 wherein $R^9$ H, methyl, benzyl or —C(O)Me.

6. The compound according to claim 4 wherein $R^{10}$ is imidazolyl.

7. The compound according to claim 1 wherein $X=CR^{11}CR^{12}R^{13}$ and $R^{11}$=H or OH; $R^{12}$=—OH, —OMe, =O, or substituted phenyl; and $R^{13}$=substituted imidazolyl.

8. A pharmaceutical composition comprising a therapeutically effective amount of a compound of claim 1 and a pharmaceutical acceptable carrier.

9. A compound according to claim 1 selected from the group consisting of:

N-Benzyl-N-[6-cyano-8-(3H-imidazol-4-ylamino)-chroman-3-yl]-methanesulfonamide;

N-[3-(Benzyl methanesulfonylamino)-6-cyanochroman-8-yl]-N-(3H-imidazol-4-yl)acetamide;

N-Benzyl-N-{6-cyano-8-[(3H-imidazol-4-yl)-methyl-amino]-chroman-3-yl}-methanesulfonamide;

N-Benzyl-N-{8-[benzyl-(3H-imidazol-4-yl)-amino]-6-cyano-chroman-3-yl}-methanesulfonamide;

N-Benzyl-N-{6-cyano-8-[hydroxy-(3-methyl-3H-imidazol-4-yl)-methyl]-chroman-3-yl}-methanesulfonamide;

N-Benzyl-N-{6-cyano-8-[methoxy-(3-methyl-3H-imidazol-4-yl)-methyl]-chroman-3-yl}-methanesulfonamide;

N-Benzyl-N-[6-cyano-8-(3-methyl-3H-imidazole-4-carbonyl)-chroman-3-yl]-methanesulfonamide;

N-Benzyl-N-{8-[(4-chloro-phenyl)-hydroxy-(3-methyl-3H-imidazol-4-yl)-methyl]-6-cyano-chroman-3-yl}-methanesulfonamide;

N-Benzyl-N-{6-cyano-8-[methyl-(3-methyl-3H-imidazol-4-ylmethyl)-amino]-chroman-3-yl}-methanesulfonamide;

N-Benzyl-N-{6-cyano-8-[methyl-(3-methyl-3H-imidazol-4-ylmethyl)-amino]-chroman-3-yl}-methanesulfonamide;

N-{6-Cyano-8-[(pyridin-4-ylmethyl)-amino]-chroman-3-yl}-N-thiophen-3-ylmethyl-methanesulfonamide;

N-[6-Cyano-8-(methyl-pyridin-4-ylmethyl-amino)-chroman-3-yl]-N-thiophen-3-ylmethyl-methanesulfonamide;

N-{6-Cyano-8-[(pyridin-3-ylmethyl)-amino]-chroman-3-yl}-N-thiophen-3-ylmethyl-methanesulfonamide;

N-[6-Cyano-8-(methyl-pyridin-3-ylmethyl-amino)-chroman-3-yl]-N-thiophen-3-ylmethyl-methanesulfonamide; and N-{6-Cyano-8-[(3H-imidazol-4-ylmethyl)-amino]-chroman-3-yl}-N-thiophen-3-ylmethyl-methanesulfonamide;

or a pharmaceutically acceptable salt thereof.

* * * * *